(12) United States Patent
Peltz et al.

(10) Patent No.: US 8,763,442 B2
(45) Date of Patent: Jul. 1, 2014

(54) COMBINED ACOUSTIC EXCITATION AND STANDOFF CHEMICAL SENSING FOR THE REMOTE DETECTION OF BURIED EXPLOSIVE CHARGES

(75) Inventors: Leora Peltz, Pasadena, CA (US); Michael A. Carralero, Huntington Beach, CA (US); Paul R. Davies, Long Beach, CA (US); Frederick L. Davis, Los Angeles, CA (US); John F. Takacs, Long Beach, CA (US)

(73) Assignee: The Boeing Company, Chicago, IL (US)

( * ) Notice: Subject to any disclaimer, the term of this patent is extended or adjusted under 35 U.S.C. 154(b) by 349 days.

(21) Appl. No.: 13/219,671

(22) Filed: Aug. 27, 2011

(65) Prior Publication Data

US 2013/0047701 A1    Feb. 28, 2013

(51) Int. Cl.
*G01N 29/14* (2006.01)
*G01N 21/70* (2006.01)

(52) U.S. Cl.
USPC .......................................... 73/24.01; 73/23.2

(58) Field of Classification Search
USPC ................. 356/318; 73/23.2, 24.01
See application file for complete search history.

(56) References Cited

U.S. PATENT DOCUMENTS

| | | | |
|---|---|---|---|
| 5,973,999 A | 10/1999 | Naff et al. | |
| 6,081,481 A * | 6/2000 | Sabatier et al. | 367/8 |
| 6,360,173 B1 | 3/2002 | Fullerton | |
| 6,417,797 B1 | 7/2002 | Cousins et al. | |
| 6,520,062 B1 | 2/2003 | Laine et al. | |
| 7,098,672 B2 * | 8/2006 | Belyakov et al. | 324/646 |
| 7,298,475 B2 * | 11/2007 | Gandhi et al. | 356/318 |
| 7,512,511 B1 | 3/2009 | Schultz et al. | |
| 7,796,264 B2 | 9/2010 | Norman | |
| 2005/0223407 A1 | 10/2005 | Fullerton et al. | |
| 2007/0091316 A1 | 4/2007 | Lal et al. | |

FOREIGN PATENT DOCUMENTS

| | | |
|---|---|---|
| EP | 1061324 | 12/2000 |
| WO | 2008051298 A2 | 5/2008 |

OTHER PUBLICATIONS

Moore, "Recent Advances in Trace Explosives Detection Instrumentation," Sensing and Imaging An International Journal, vol. 8, Mar. 2007, pp. 9-38.

Waschl, "A Review of Landmine Detection Technologies," Report No. DSTO-TR-0113, Aeronautical and Maritime Research Laboratory of the Commonwealth of Australia, Dec. 1994.

(Continued)

*Primary Examiner* — Lisa Caputo
*Assistant Examiner* — Punam Roy
(74) *Attorney, Agent, or Firm* — Clifford G. Cousins

(57) ABSTRACT

In representative embodiments, a system includes an acoustic emitter, a controller, an optical sensor, and an indicator for indicating a detection of a predetermined trace chemical vapor by the optical sensor. The acoustic emitter is positioned at a predetermined distance above the ground surface and configured to project a beam of acoustic energy toward the ground surface with a variable angle of incidence $\alpha$. The controller is configured to control the acoustic emitter to vary the angle of incidence of the acoustic beam within the variable angle of incidence $\alpha$, while the optical sensor is configured for standoff sensing of a trace chemical vapor proximate the ground surface. Excitation of the ground surface, particularly at a critical angle of incidence $\beta$, causes the release of trace chemical vapors from a buried source and the soil into the air above the buried source.

20 Claims, 8 Drawing Sheets

(56) References Cited

OTHER PUBLICATIONS

Donskoy et al., "Nonlinear seismo-acoustic land mine detection and discrimination", J. Accoust. Soc. Am., vol. 111 No. 6, Jun. 2002, pp. 2705-2714.

Xiang et al., "An experimental study on antipersonnel land mine detection using acoustic-seismic coupling", J. Accoust. Soc. Am., vol. 113 No. 3, Mar. 2003, pp. 1333-1341.

Valeau et al., "Development of a time-frequency representation for acoustic detection of buried objects", J. Accoust. Soc. Am.116 vol. 5, Nov. 2004, pp. 2984-2995.

Xiang et al., "Acoustic-to-Seismic Landmine Detection Using a Continuously Scanning Laser Doppler Vibrometer", Proc. of SPIE vol. 5089 (2003), Detection and Remediation Technologies for Mines and Minelike Targets VIII, pp. 591-595.

Sabatier et al., "High Frequency A/S Coupling for AP Buried Landmine Detection using Laser Doppler Vibrometers", Proc. of SPIE vol. 5415 (2004), Detection and Remediation Technologies for Mines and Minelike Targets IX, pp. 35-41.

Scott et al, "Experimental Model for a Seismic Landmine Detection System", IEEE Transactions on Geoscience and Remote Sensing, vol. 39 No. 6, Jun. 2001, pp. 1155-1164.

Anderson et al., "Ultra-wideband beamforming in sparse arrays", IEEE Proceedings—H, vol. 138 No. 4, Aug. 1991, pp. 342-346.

"Seismic Source White Paper", The Boeing Company, Aug. 24, 2010, pp. 1-20.

Dogariu et al., "High gain backward lasing in air," Science, vol. 331 No. 6016, Jan. 2011, pp. 442-445.

Van Den Heuvel, "Laser-induced acoustic landmine detection with experimental results on buried landmines," Proceedings of SPIE, vol. 5415, Sep. 2004, pp. 51-60.

Singh, "Sensors—An effective approach for the detection of explosives," Journal of Hazardous Materials, vol. 144, Jun. 2007, pp. 15-28.

Combined Search and Examination Report, Application No. GB 1215257.5 (Nov. 30, 2012).

\* cited by examiner

Source: D.S. Moore, *Recent Advances in Trace Explosives Detection Instrumentation*, Sensing and Imaging, Vol. 8 No. 1, p. 11 (2007).

COMBINED ACOUSTIC EXCITATION AND STANDOFF CHEMICAL SENSING FOR THE REMOTE DETECTION OF BURIED EXPLOSIVE CHARGES

FIELD

The present disclosure is directed to systems and methods for the remote detection of buried, low-volatility chemicals and, in particular, systems and methods for the remote detection of buried explosive charges in devices such as landmines and improvised explosive devices.

BACKGROUND

Landmines and mine-like improvised explosive devices ("IEDs") are weapons that are typically buried under the soil surface or other debris in order to avoid detection. The devices generally include an initiator, a detonator, and a bulk explosive charge. The initiator may be a built-in trigger such as a pressure plate, a magnetic sensor, or an acoustic sensor, or, particularly in the case of IEDs, a receiver for a remote triggering device such as a detonator box, a phototrigger, or a cellular phone. The detonator is generally one of a plethora of small primary explosive devices, such as a blasting cap, that can be embedded within or placed in direct contact with the bulk explosive charge. The combined explosives are generally enclosed within a housing to protect them prior to detonation. This housing could be variously constructed from metal (for convenience, to shape the force of the explosive charge, or to serve as a source of fragmentation projectiles), plastic (to avoid detection by metal detection technologies), or, particularly in the case of IEDs, convenience materials such as glass or wood. The least variable element in these devices tends to be the bulk explosive charge, which is generally a secondary explosive, such as TNT (trinitrotoluene), RDX (hexahydro-1,3,5-trinitro-1,3,5-triazine), or PETN (pentaerythritol tetranitrate), but in the case of IEDs may sometimes be a less stable primary explosive, such as TATP (triacetone triperoxide) or TNP (trinitrophenol, also known as "picric acid"). While explosives obtained from some commercial sources may contain a semi-volatile chemical taggant, such as EGDN (ethylene glycol dinitrate), DMDNB (2,3-dimethyl-2,3-dinitrobutane), or mononitrotoluenes (o-MNT and/or p-MNT), military-grade and "homebrewed" explosives will lack such taggants, making the detection of an explosive compound itself the most reliable method for detecting a buried landmine or IED.

In landmines and mine-like IEDs, the devices are usually buried within about 0.5 meters of the ground surface, with the typical depth varying from centimeters for small anti-personnel devices to tens of centimeters for larger anti-vehicular devices. Thus, both ground-penetrating and surface sensing technologies have been employed to detect these devices. For example, the bulk explosive charge, as well as any initiator, detonator, and housing, will generally have a different acoustic impedance from the soil or debris in which it is buried, reflecting at least a portion of the energy emitted by an acoustic detection system away from the buried device. As shown in FIG. 1, where solid lines represent empirical measurements and dashed lines represent extrapolations of the empirical measurements across the illustrated temperature range, most explosive materials will also have a slight but non-negligible vapor pressure in comparison to normal atmospheric pressure (760 Ton or $10^9$ ppbv, located at approximately the top of the graph), so that trace amounts of the explosive charge will tend to disperse into the soil and air above a buried device.

Acoustic technologies have previously been applied to the problem of landmine detection, but in the main only through an analysis of the acoustic energy reflected as a result of the aforementioned difference in acoustic impedance. In a first technique, a loudspeaker emits an acoustic pulse over a suspected device, a microphone array measures the reflected acoustic energy, and the microphone data is rapidly analyzed to determine whether the array has detected a significant deviation from background acoustic reflections, indicating a buried object. See, for example, John A. Waschl's discussion of differential acoustic reflection technologies in *A Review of Landmine Detection Technologies*, Report No. DSTO-TR-0113, published by the Aeronautical and Maritime Research Laboratory of the Commonwealth of Australia (1994). In a second technique, a loudspeaker (or, potentially, a laser) generates an acoustic pulse near a suspected device, a laser Doppler device measures the motion of the ground surface caused by the acoustic pulse and any reflected acoustic energy, and the laser Doppler data is rapidly analyzed to detect anomalous surface motion caused by a change in acoustic impedance or acoustic reflection, indicating a buried object. See, for example, J. C. van den Heuvel et al.'s disclosure of a laser Doppler vibrometer system in *Laser-induced Acoustic Landmine Detection with Experimental Results on Buried Landmines*, Proceedings of SPIE, Vol. 5415, pp. 51-60 (2004). The second technique is a significant advance over the first, since the laser Doppler device can comparatively rapidly scan an area from a distance, permitting the standoff detection of shallowly buried objects within an intended path of travel. However, while these technologies can detect buried landmines and IEDs, they are also susceptible to "false targets"—i.e., they tend to detect all buried objects that appear acoustically similar to a landmine or other target device, regardless of whether that object is an explosive device, a decoy device, or merely buried litter.

Light-based standoff chemical sensing technologies, such as spectroscopy, have also been applied to the problem of landmine detection, but are poorly suited for detecting buried, low-volatility explosives since they typically seek to detect trace chemical vapors in the most dynamic part of the environment near a buried device—the air above the ground surface. See, for example, Suman Singh's discussion of laser-induced breakdown spectroscopy ("LIBS") in *Sensors—An Effective Approach for the Detection of Explosives*, Journal of Hazardous Materials, Vol. 144, pp. 15-28 (2007). Scientists and engineers seeking to improve standoff explosives detection technology have recently begun to combine light-based standoff chemical sensing technologies with heating techniques in order to increase the concentration of trace chemical vapors in the air and improve the effective sensitivity of their systems. An example of such a combination, disclosed in U.S. Pat. No. 7,796,264, uses a remote heat source such as a microwave beam to heat a target material in order to increase the vapor pressure of the target's constituent materials and consequently the concentrations of chemical vapors found in the air above the target. However, while such a system could be modified to sequentially heat the ground surface in order to search for an unseen and buried explosive device, such a modified system would need to heat large areas of the ground surface, and the speed of the modified system would be limited by the power that could be projected to heat an intended path of travel.

As a result, the applicants have perceived a need for an enhanced chemical sensing system that is better suited for use with buried, low-volatility chemicals, and in particular better suited for standoff use in the remote detection of buried explosive charges such as those found in landmines and IEDs. Such a system should be reasonably selective for the chemical species of interest, with a lower false positive rate than known acoustic detection technologies, but require less power than spectroscopic systems combined with wide-area heating techniques.

SUMMARY

In a first aspect, a system for detecting low-volatility chemicals buried below a ground surface, including an acoustic emitter, a controller, an optical sensor, and an indicator. The acoustic emitter is positioned at a predetermined distance above the ground surface and configured to project a beam of acoustic energy toward the ground surface with a variable angle of incidence α. The controller is configured to control the acoustic emitter to vary the angle of incidence of the acoustic beam within the variable angle of incidence α, while the optical sensor is configured for standoff sensing of a trace chemical vapor proximate the ground surface. Excitation of the ground surface, particularly at a critical angle of incidence β, causes the release of trace chemical vapors from a buried source and the soil into the air above the buried source. The indicator indicates a detection of a predetermined trace chemical vapor by the optical sensor.

In a second aspect, a method for detecting low-volatility chemicals buried below a ground surface includes the steps of (a) positioning an acoustic emitter at a predetermined distance d above the ground surface; (b) emitting an acoustic beam from the acoustic emitter to ensonify the ground surface, the acoustic beam being emitted at at least one angle of incidence so as to generate a surface wave; (c) operating an optical sensor to detect at least a predetermined trace chemical vapor proximate the ensonified ground surface; and (d) indicating, if the predetermined trace chemical vapor is detected, that the optical sensor has detected the buried low-volatility chemical. The at least one angle of incidence may be a predetermined angle of incidence or a variable angle of incidence α selected to encompass a critical angle of incidence β for acoustic-to-seismic coupling into a surface wave.

In a third aspect, a method for detecting low-volatility chemicals buried below a ground surface includes the steps of (a) positioning an acoustic emitter at a predetermined height above the ground surface; (b) estimating a critical angle of incidence β, with the estimate being based upon at least one measured or observed parameter; (c) emitting an acoustic wave from the acoustic emitter through air to ensonify the ground surface, the acoustic beam being emitted at the estimated critical angle of incidence β toward the ground surface; (d) scanning an optical sensor across the ground surface to detect a trace chemical vapor in the air above the ground surface; and (e) indicating, if a predetermined trace chemical vapor is detected, that the optical sensor has detected the buried low-volatility chemical. The estimated critical angle of incidence β may determined one or more of a number of measurements and observations, including the speed of sound in air, the speed of sound in the subsurface, soil type, soil water content, soil sand, clay, and silt fractions, and the amplitude of surface waves generated at other angles of incidence.

DETAILED DESCRIPTION

Figure 1:
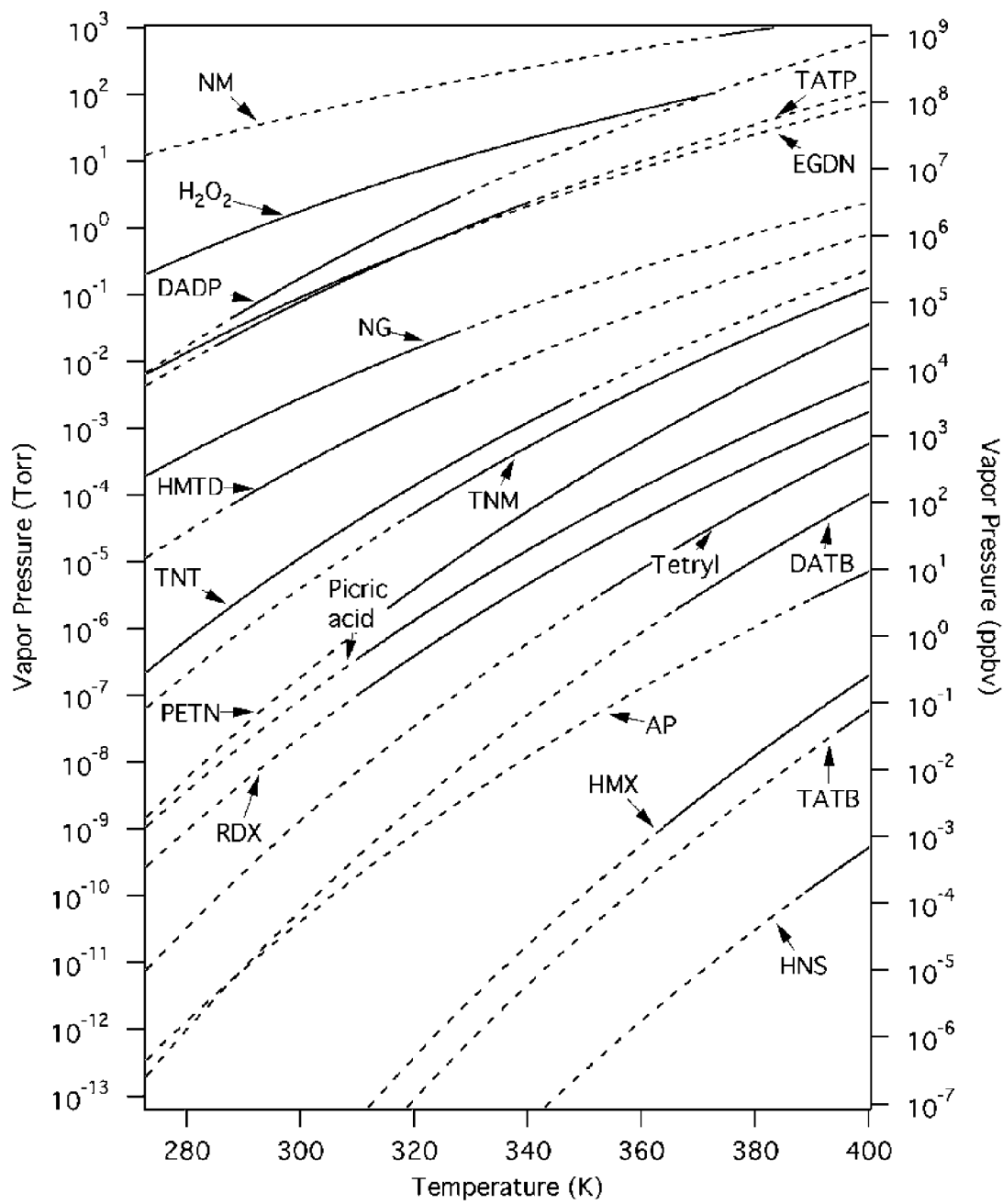
FIG. 1 is a graph of several curves of vapor pressure versus temperature for various bulk explosives.
Figure 2A:
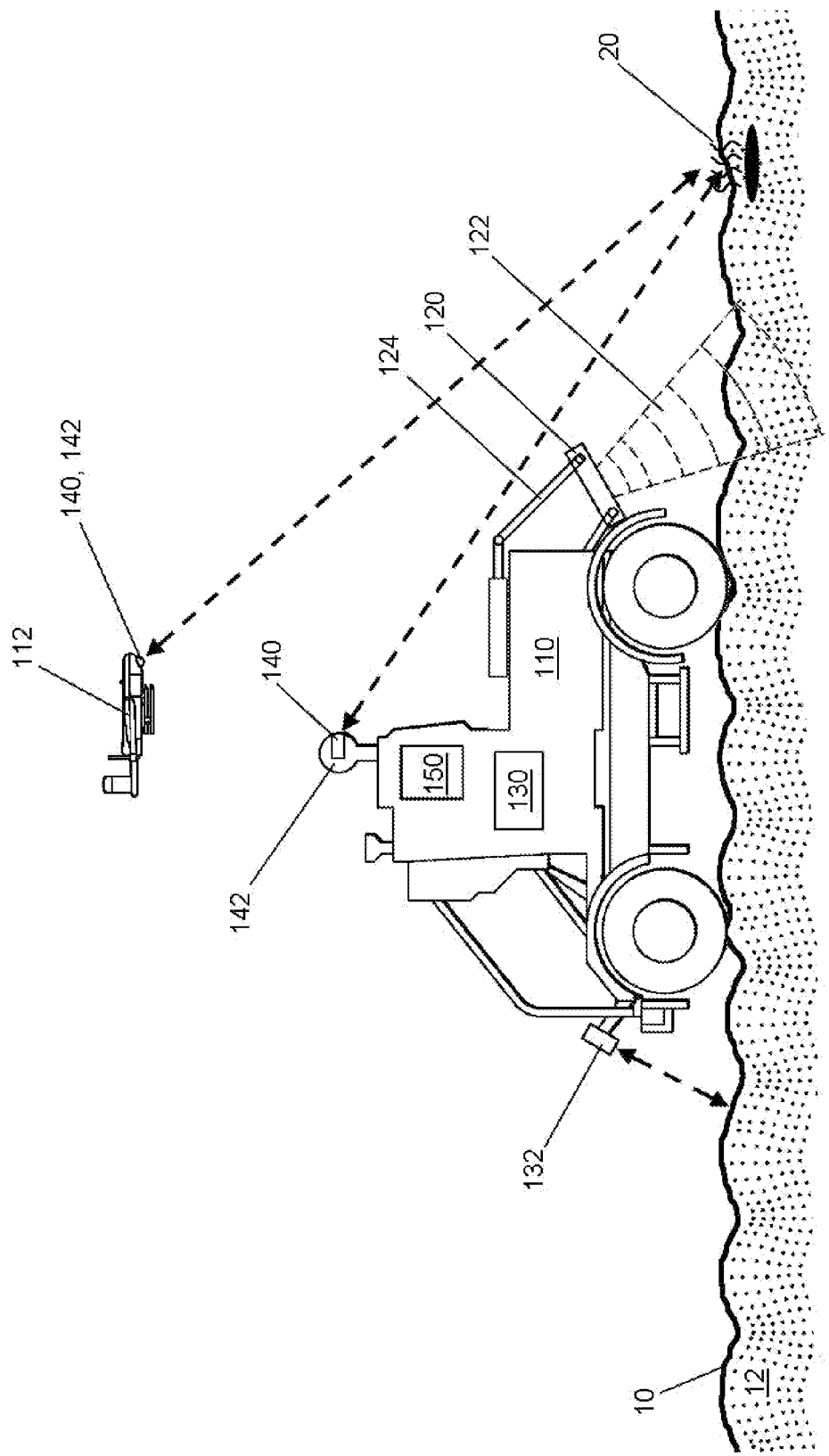
FIG. 2A is a schematic diagram of an aspect of the standoff chemical sensing system.
Figure 2B:
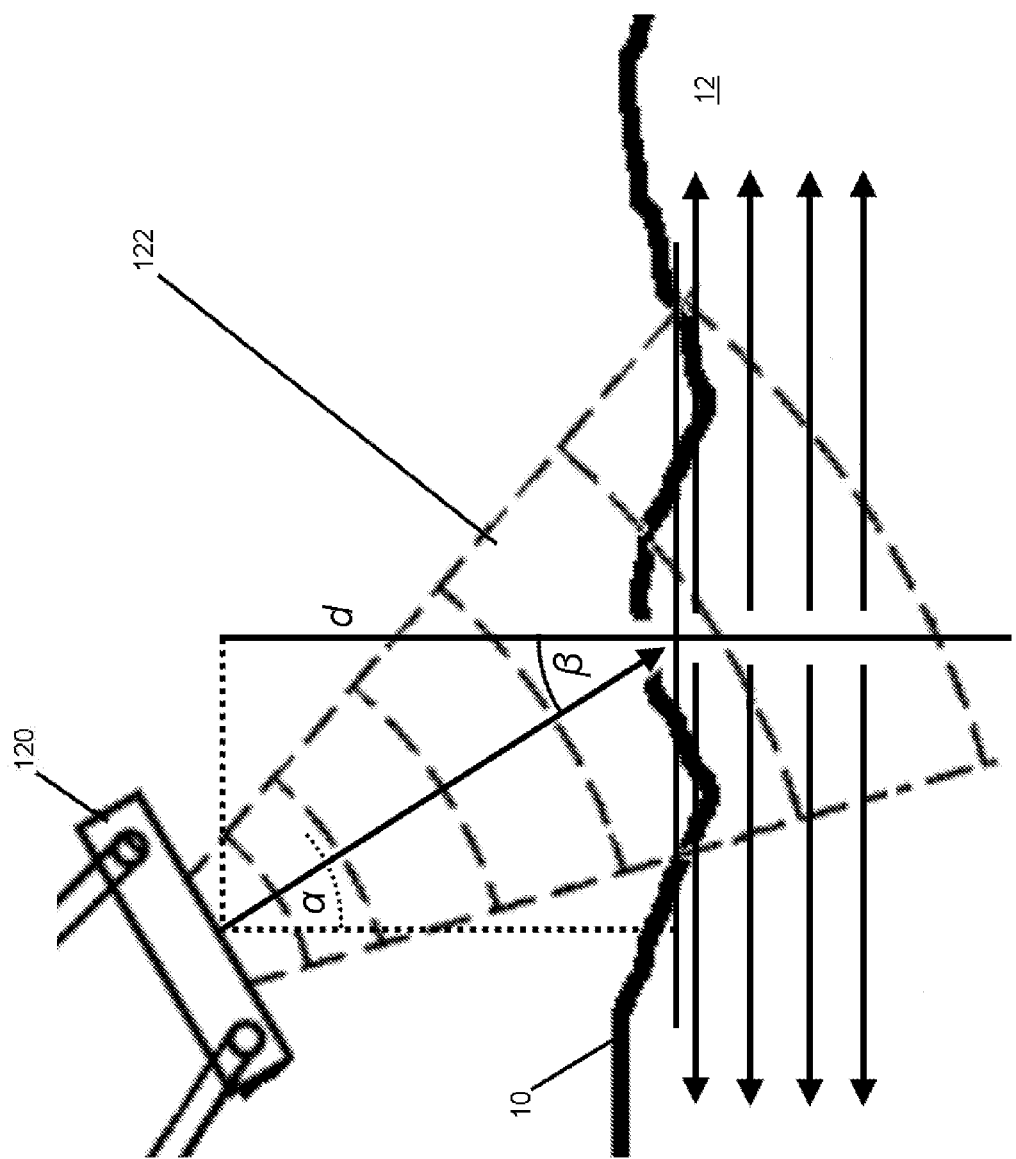
FIG. 2B is an abstracted diagram of region 2B of FIG. 2A.

With initial reference to FIG. 2A, an aspect of an improved standoff chemical sensing system 100 combines an acoustic emitter 120 for the acoustic excitation of the ground surface 10 with an optical sensor 140 for standoff sensing of trace chemical vapors 20 proximate the ground surface 10. The acoustic emitter 120 may be a directional emitter, such as a directional loudspeaker or sonic cannon, or a directionally agile emitter configured to electronically steer acoustic energy, such as a line array loudspeaker. The acoustic emitter 120 is positioned at a predetermined distance, d, above the ground surface 10. For example, the predetermined distance d may range from about 30 cm (for adequate ground clearance) to about 150 cm (to limit attenuation and beam spreading). The acoustic emitter 120 is also configured to project a beam 122 of acoustic energy toward the ground surface 10 with a variable angle of incidence, α (illustrated as a corresponding congruent angle for sake of clarity), with respect to the local ground surface 10 so as to generate a Rayleigh or so-called surface wave. The variable angle of incidence α ranges from a maximum angle of incidence to a minimum angle of incidence, with the respective angles being selected to encompass a critical angle of incidence for acoustic-to-seismic coupling into a surface wave within various soils. This variable angle of incidence is a consequence of Snell's law, $$\frac{\sin(\theta_1)}{c_1} = \frac{\sin(\theta_2)}{c_2}, \tag{1}$$

where $\theta_1$ and $\theta_2$ are the angles of incidence and refraction for a pressure pulse transitioning between the air and the immediate subsurface, and $c_1$ and $c_2$ are the speeds of sound in the air and the immediate subsurface, respectively. The speed of sound in a subsurface soil layer will vary depending upon soil type, soil moisture content, and other soil parameters, so that the true critical angle of incidence for acoustic-to-seismic coupling will vary from time to time and place to place. As discussed further below, the angle of incidence of the acoustic beam 122 is preferably adjusted to or oscillated around an estimated critical angle of incidence, β, during operation of the system; however the applicants have found that, in general, a variable angle of incidence with a minimum angle of about 25 degrees and a maximum angle of about 37 degrees is suitable for typical soil types and soil conditions.

In a first embodiment of the system, where the acoustic emitter 120 is a directional emitter, the acoustic emitter may include a motorized mount 124 configured to alter the tilt of the acoustic emitter 120 with respect to the ground surface 10 so as to vary the angle of incidence α of the acoustic beam 122. In a variation of this first embodiment, the motorized mount 124 may be further configured to oscillate the tilt of the acoustic emitter 120 with respect to the ground surface 10 within the variable angle of incidence α. In such a variation, the oscillation may encompass the entire variable angle of incidence α or, more preferably, be limited to a predetermined subrange of the variable angle of incidence, γ. An oscillation which is limited to a predetermined subrange of potential angles permits more frequent ensonification of the ground surface at the true critical angle of incidence, but requires an estimate of the critical angle of incidence β that is based upon observed or measured soil properties in order to properly direct the acoustic beam 122. In a second embodiment of the system, where the acoustic emitter 120 is a directionally agile emitter, the acoustic emitter 120 may be configured to electronically steer the acoustic beam 122 within a vertical plane so as to vary the angle of incidence α of the acoustic beam 122. In a variation of this second embodiment, the acoustic emitter 120 may be configured to oscillate the acoustic beam 122 within a similar predetermined subrange γ. In such a variation, and depending upon the capabilities of the directionally agile emitter, the acoustic emitter 120 may also include a motorized mount 124 configured to alter the tilt of the acoustic emitter 120 with respect to the ground surface 10 in order to provide for gross adjustment within the variable angle of incidence α in addition to oscillation within the predetermined subrange γ. Motorized mounts enabling the tilting of an object and line array loudspeaker systems with electronically steerable beams are known within the prior art, so that specific implementations of these systems will not be discussed or illustrated herein. The acoustic emitter 120 is preferably mounted on a mobile platform 110, such as a motorized vehicle or remote-controlled mobile platform, so that it can be easily advanced along an intended path of travel.

A controller 130 is operatively connected to the acoustic emitter 120. The controller 130 is configured to control the acoustic emitter 120 to vary the angle of incidence of the acoustic beam 122 within the variable angle of incidence α. In the first embodiment, the controller 130 may be configured to operatively control the motorized mount 124, whereas in the second embodiment, the controller 130 may be configured to operatively control the emission of the acoustic beam 122, e.g., by varying the acoustic signal emitted from the individual elements of a line array loudspeaker. The controller 130 is preferably configured to estimate a critical angle of incidence β for acoustic-to-seismic coupling of the acoustic beam 122 to the subsurface soil layer 12, and to control the acoustic emitter 120 to project the acoustic beam 122 toward the ground surface 10 at the estimated critical angle of incidence β. In the variation of the first embodiment introduced above, the controller 130 may subsequently control the motorized mount 124 to oscillate the acoustic emitter 120, and consequently the acoustic beam 122, within a predetermined subrange of the variable angle of incidence α centered around the estimated critical angle of incidence β. In the variation of the second embodiment introduced above, the controller 130 may subsequently control the acoustic emitter 120 to oscillate the acoustic beam 122 within a predetermined subrange of the variable angle of incidence α centered around the estimated critical angle of incidence β.

The critical angle, as used in the present application, is defined as the angle of incidence in which an acoustic beam or pressure wave propagating in the air strikes an area of incidence, and optimally couples into a Rayleigh or so-scalled "surface wave." In contrast to body wave modes which propagate primarily in a direction perpendicular to the soil surface, such as P-waves (longitudinal waves) and S-waves (transverse waves), a surface wave manifests as a combination of wave modes (longitudinal and transverse) sustained by reflections of acoustic energy both at and beneath the ground surface. Because of this nature, surface waves are generally confined near the ground surface and decay exponentially with depth, with the first half wavelength of depth containing most of the energy of the surface wave. This confinement enhances surface propagation in comparison to a body wave, so that if the source of the wave is abstracted as a point source, the in-plane amplitude of a surface wave decays in inverse proportion to the square root of distance from the point source, rather than in inverse proportion to the distance from the point source as would a spherical wave front. Advantageously, surface waves will follow the ground surface over gradual rises and through gradual depressions, enabling the excitation of the immediate subsurface along a path of travel without need to account for acoustic shadowing due to minor topographic obstructions. The critical angle for acoustic-to-seismic coupling of soil can be estimated by $$\frac{\sin(\theta_1)}{c_1} = \frac{\sin(90^0)}{c_2}, \text{ or } \beta = \theta_1 = \sin^{-1}\left(\frac{c_1}{c_2}\right) \tag{2}$$

where the angle of refraction is a 90 degree angle, parallel to the local ground surface, and the angle of incidence causes an optimal conversion of the incident acoustic beam into a surface wave. In practical application, this very simplified estimate may require an empirical correction factor due to mode conversion, the inhomogeneity in the soil composition in the area of incidence, the reflection of acoustic energy projected at an angles of incidence greater than the critical angle due to beam spreading, the refraction of acoustic energy projected at an angle of incidence less than the critical angle due to beam spreading (which may still contribute to a surface wave), and the like. Such a factor may be stored in controller 130.

Figure 3A:
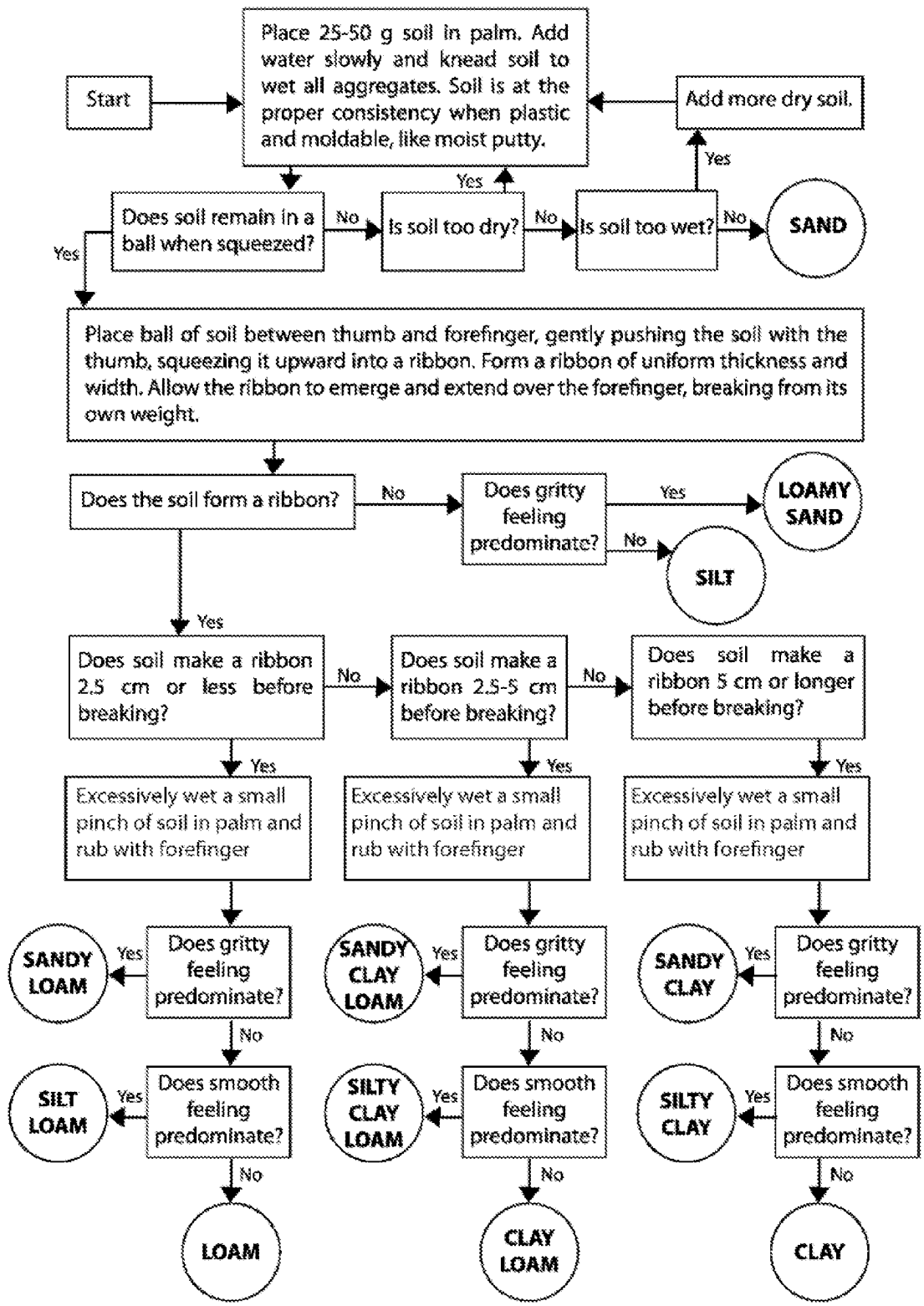
FIG. 3A is a block diagram of a known method for determining soil type by feel.
Figure 3B:
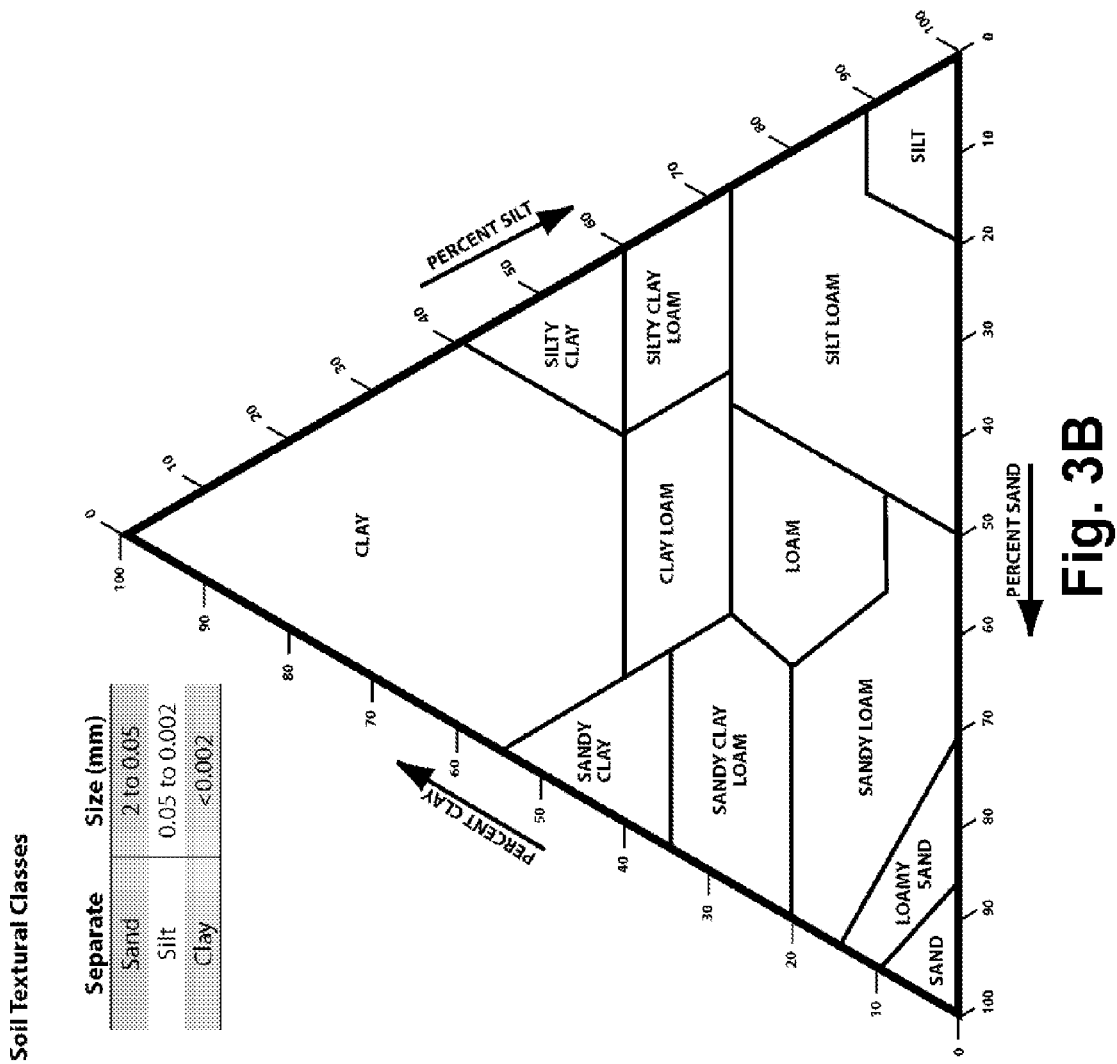
FIG. 3B is a graphical soil classification chart.

In a first implementation of the system, the controller 130 may be configured to receive at least one measured parameter, such as a speed of sound in air or a speed of sound in the immediate subsurface, which may be used to estimate the critical angle of incidence β. For example, the speed of sound could be measured by deploying a microphone and geophone at a known distance from the acoustic emitter 120 and measuring the time to the arrival of the first waves from a single acoustic pulse. In a second implementation of the system, the controller 130 may be configured to receive at least one observed soil parameter, such as soil type or soil water content, which may correlated to a speed of sound using known geophysical methods. In such an implementation, the controller 130 may be programmed with, for example, reference values for the density, bulk modulus, and speed-moisture curve of various observable soil types, which may then be used to estimate the critical angle of incidence β. For example, FIGS. 3A-3B illustrate a known soil type estimation method adapted from S. J. Thien's *A Flow Diagram for Teaching Texture by Feel Analysis*, Journal of Agronomic Education, Vol. 8 pp. 54-55 (1979). In a variation of the second implementation, the controller 130 may be configured to receive measured, rather than observed, soil parameters such as soil water content, soil sand fraction, soil silt fraction, and soil clay fraction obtained through the use of soil analysis equipment. The former observed soil types may be related to measured soil fractions by, for example, a known classification system graphically depicted in FIG. 3B as a soil textural triangle. In a third implementation of the system, the controller may be configured to receive hyperspectral or multispectral imagery of the ground surface, and to analyze this imagery to measure at least one soil parameter such as soil type or soil water content. Systems and methods employing hyperspectral or multispectral analysis of the soil surface to determine aspects of soil type or near-surface soil water content or are known and discussed within relevant aerospace and agricultural science sources, so that specific implementations of these systems will not be discussed or illustrated herein. The reader will appreciate that various combinations of these exemplary implementations are possible and indeed contemplated by the present disclosure. Depending upon the degree of human interaction involved in receiving the relevant parameters, i.e., whether the air and/or water parameters are measurements obtained from automated instrumentation, geographically registered digital databases, or measurements and observations input by a human operator, the controller 130 may operatively control the acoustic emitter 120 to project the acoustic beam 122 at or around the estimated critical angle of incidence β in real time, in response to periodic updates, or in response to an initial configuration/calibration.

In yet another implementation, the controller 130 may be configured to estimate the critical angle of incidence β by serially adapting a prior estimate of the critical angle of incidence β in response to a measured parameter—surface wave response. The system 100 may include a ground motion detector 132, such as a portable seismometer, configured to measure the amplitude of surface waves generated by the acoustic emitter 120 and operatively connected to the controller 130 in order to communicate the resultant measurements. In one variation, the controller 130 may operate the acoustic emitter 120 at a default first estimate of critical angle β, obtain a first measurement of surface wave amplitude from motion detector 132, operate the acoustic emitter 120 at a similar but different (e.g., 3-5 degree different) second estimate of critical angle β, obtain a second measurement of surface wave amplitude from motion detector 132, and subsequently repeat the estimate-and-measure cycle using numerical modeling to progress toward a critical angle of incidence resulting in a maximum value of surface wave amplitude. In a second variation, the controller may operate the acoustic emitter 120 in a similar manner, but use a first estimate and a similar but different second estimate based upon measured and/or observed parameters, such as those described in the first through third implementations. In particular, a ground motion detector 132 such as a laser Doppler vibrometer may be employed, not to acoustically detect a buried object, but instead to enable a near-real time adjustment of the estimated critical angle of incidence β, with the estimated value varying around a true critical angle of incidence so as to optimize the coupling of the acoustic beam 122 into the desired surface wave at essentially any time. In this implementation, the estimated critical angle of incidence β and/or the surface wave response may be stored in the controller 130, along with location information obtained from a GPS unit, for comparison at a later date. The estimated critical angle of incidence β and/or the surface wave response obtained when a location is revisited may subsequently be compared against the estimated critical angle of incidence β and/or the surface wave response stored in the controller 130 to identify discrepancies between the measured and previously stored surface wave response that may indicate a disturbance of the subsurface caused by the concealment of a landmine or IED.

The optical sensor 140 of the chemical sensing system 100 may be an active optical sensor, such as a Differential Absorption LIDAR (DIAL) sensor, a Stimulated Raman scattering Spectroscopy (SRS) or Coherent anti-Stokes Raman scattering Spectroscopy (CARS) sensor, a Laser-Induced Fluorescence (LIF) or Laser-Induced Breakdown Spectroscopy (LIBS) sensor, or other light-emitting and detecting sensor systems. The optical sensor 140 of the chemical sensing system 100 may alternately be a passive optical sensor, such as a hyperspectral sensor, a multispectral sensor, or a differential reflection spectroscopy sensor. In particular, the system and method of the present disclosure may be well suited for use with a high gain, UV-pumped, backward lasing system developed by Arthur Dogariu et al. of Princeton University and disclosed in *High Gain Backward Lasing in Air*, Science, Vol. 331 No. 6016 pp. 442-445. The Princeton system uses a 100 picosecond remote pump laser to generate a 226 nm (UV) wavelength beam that is emitted through a focusing lens. At the focal point of the lens, the laser drives a dissociation of atmospheric oxygen and excites one of the resulting oxygen molecule fragments (an oxygen atom radical), producing a stimulated emission at 845 nm (near-IR) which propagates both forward and backward along the path of the pump laser beam. This backward lasing near-IR beam can subsequently be used to identify chemical species which may be present in the return path, allowing for single-sided detection of chemical species using a coherent radiation source rather than a non-directional spontaneous light emission or specularly reflected laser light.

The optical sensor 140 may be configured to detect a predetermined trace chemical vapor, or alternately configured to detect a plurality of trace chemical vapors, passing that information to a controller, such as controller 130, programmed with a library of chemical signatures including the signature of the predetermined trace chemical vapor. The optical sensor may be configured to detect trace chemical vapors emitted from a buried, low-volatility chemical or chemicals and, preferably, to detect trace chemical vapors from a buried explosive charge comprised of a low-volatility chemical explosive such as those introduced in the background of the disclosure. Depending upon the specificity of the optical sensor 140, the optical sensor 140, the controller (e.g., controller 130), or both components may signal the detection of the predetermined trace chemical vapor. An indicator 150 operatively connected to the optical sensor 140, either directly or via a controller such as controller 130, may indicate the presence of the predetermined trace chemical vapor, the concentration or relative concentration of the predetermined trace chemical vapor, the relative location of the predetermined trace chemical vapor, and the like. The indicator 150 may be, for example, a warning light, a text display, a graphical display, or an audible alert.

Figure 4:
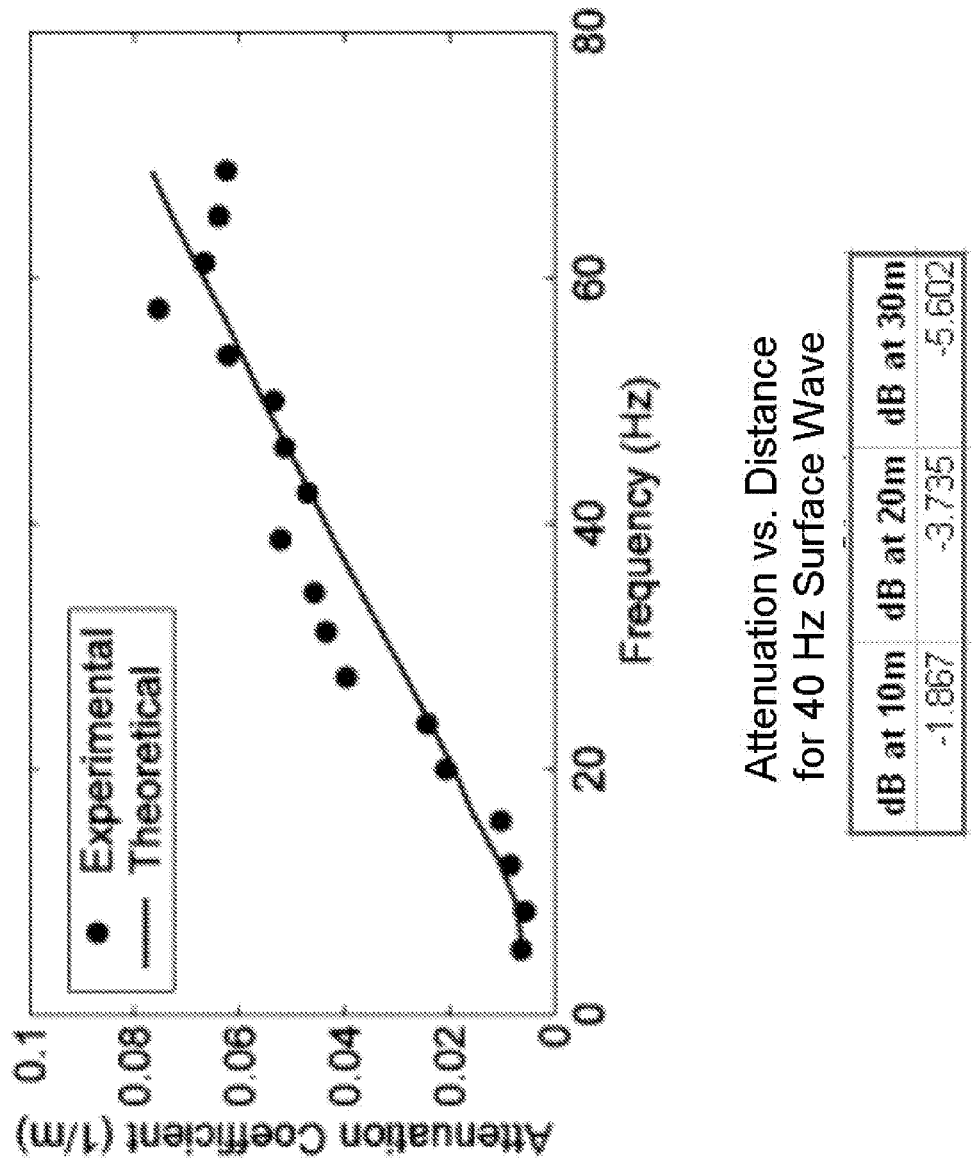
FIG. 4 is a graph of surface wave attenuation in an exemplary loam soil type.

The optical sensor 140 may be mounted on the mobile platform 110 and combined with a motorized scanning device 142 to scan a path of travel as the mobile platform 110 is advanced. Alternately, the optical scanner need not be mounted on this first mobile platform 110, but may be mounted and combined with a motorized scanning device 142 on a separate, second mobile platform 112, such as a separate motorized vehicle, remote-controlled ground-mobile platform, or remote-controlled air-mobile platform. Excitation of the ground surface 10 by the acoustic emitter 120 can create a comparatively large area of effect. For example, as shown in FIG. 4, a surface wave generated at a frequency of 40 Hz will attenuate by approximately 6 dB, or lose roughly 75% of its initial power, at a distance of 30 meters in a silty loam subsurface soil layer. Separation of the optical sensor 140 from the acoustic emitter 120 by mounting the former on a second mobile platform 112 may advantageously enable optical sensors with lesser detection ranges to advance ahead of the first platform, or act as one of a number of semi-autonomous optical sensors 140 to examine and clear a broad path of travel. Communication and control between the respective mobile platforms 110, 112, for example, for the operative connection between the optical sensor 140 and the indicator 150, may be maintained by a hardwired tether or wireless radio link.

Figure 5:
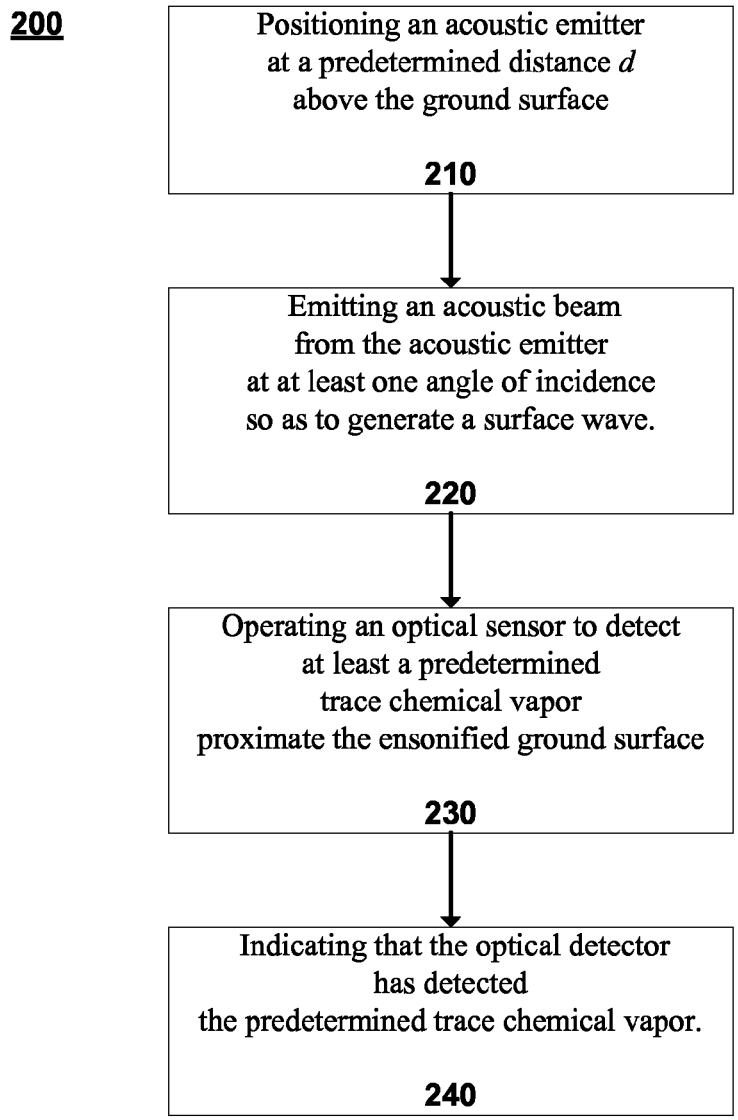
FIG. 5 is a block diagram of an aspect of the disclosed method for standoff chemical sensing.

With reference to FIG. 5, an aspect of an improved standoff chemical sensing method 200 includes the following steps:

First, 210, positioning an acoustic emitter 120 at a predetermined distance d above the ground surface 10. For example, the predetermined distance d may range from about 30 cm (for adequate ground clearance) to about 150 cm (to limit attenuation and beam spreading).

Second, 220, emitting an acoustic beam 122 from the acoustic emitter 120 to ensonify the ground surface 10, the acoustic beam 122 being emitted at at least one angle of incidence so as to generate a surface wave. In a first implementation of this aspect, the at least one angle of incidence may be a predetermined angle of incidence, such as a known critical angle of incidence at that location. In a second implementation of this aspect, the at least one angle of incidence may be a variable angle of incidence $\alpha$ selected to encompass a critical angle of incidence $\beta$ for acoustic-to-seismic coupling into a surface wave within at least one predetermined soil type. For example, the variable angle of incidence $\alpha$ may range between a minimum angle of about 25 degrees and a maximum angle of about 37 degrees.

Third, 230, operating an optical sensor 140 to detect at least a predetermined trace chemical vapor proximate the ensonified ground surface 10. More specifically, the optical sensor 140 may be an active or passive optical sensor configured to exclusively detect the chemical signature of the predetermined trace chemical vapor; or, alternately, an active or passive optical sensor configured to detect a plurality of trace chemical vapors, and connected to a controller, such as controller 130, programmed with a library of chemical signatures including the signature of the predetermined trace chemical vapor.

Fourth, 240, indicating, when appropriate, that the optical sensor 140 has detected the predetermined trace chemical vapor.

In a first variation of this aspect, the emitting step may include oscillating the acoustic beam 122 throughout the variable angle of incidence $\alpha$. In a second variation of this aspect, the emitting step may include oscillating the acoustic beam 122 through a predetermined subrange of the variable angle of incidence, $\gamma$. As discussed above, an oscillation which is limited to a predetermined subrange of potential angles permits more frequent ensonification of the ground surface at the true critical angle of incidence, but requires an estimate of the critical angle of incidence $\beta$ in order to properly direct the acoustic beam 122. This estimating step may be performed manually using an approach such as that used in equation (2), or automatically by a controller 130 in response to one or more of the inputs described in paragraphs 0022 and 0023, above.

Figure 6:
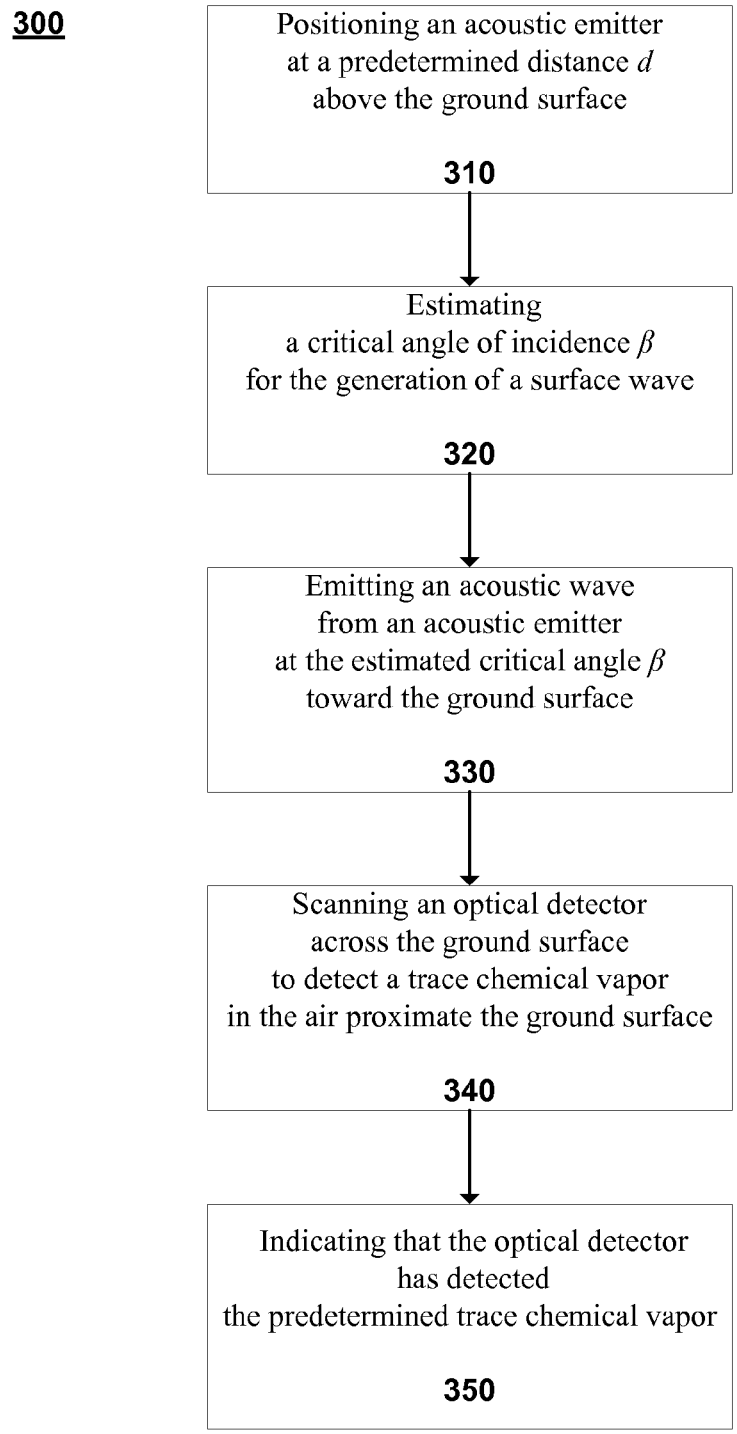
FIG. 6 is a block diagram of another aspect of the disclosed method for standoff chemical sensing.

With reference to FIG. 6, another aspect of the improved standoff chemical sensing method 300 includes the following steps:

First, 310, positioning an acoustic emitter 120 at a predetermined distance d above the ground surface 10. For example, the predetermined distance d may range from about 30 cm (for adequate ground clearance) to about 150 cm (to limit attenuation and beam spreading).

Second, 320, estimating a critical angle of incidence $\beta$ for the generation of a surface wave, with the estimate being based upon at least one measured or observed parameter. In a first implementation of this aspect, the parameter may be a measured parameter such as such as a measured speed of sound in air, a measured speed of sound in the subsurface, a measured soil water content, a measured soil sand fraction, a measured soil clay fraction, or a measured soil silt fraction. In a second implementation of this aspect, the parameter may be an observed parameter such as an observed soil type or an observed soil water content. In a third implementation of this aspect, the parameter may be a measured surface wave amplitude, with the estimating step including an estimate-and-measure cycle using numerical modeling to progress toward a critical angle of incidence resulting in a maximum value of surface wave amplitude. The estimation step in such an instance may be performed as an initial calibration prior to any search and detection activity or, preferably, as a real time estimation step contemporaneously with search and detection activity.

Third, 330, emitting an acoustic wave from an acoustic emitter 120 at the estimated critical angle of incidence $\beta$ toward the ground surface 10.

Fourth, 340, scanning an optical sensor 140 across the ground surface 10 to detect a trace chemical vapor in the air proximate the ground surface 10. As indicated in step 230 of the prior aspect, this detection may be specific and particular to the optical sensor 140, or non-specific and made in combination with a controller, such as controller 130, programmed with a library of chemical signatures.

Fifth, 350, indicating, when appropriate, that the optical sensor 140 has detected the predetermined trace chemical vapor.

In a variation of this aspect, the emitting step may include oscillating the acoustic beam 122 through a range of angles of incidence, $\gamma$, centered around the estimated critical angle of incidence $\beta$. Such an oscillation advantageously permits periodic ensonification of the ground surface at the true critical angle of incidence even if the estimated critical angle of incidence $\beta$ is materially different, which would be expected to reduce power at a given range due to greater reflection of the incident acoustic energy or greater dissipation of the incident acoustic energy as a body wave.

The combined acoustic excitation and standoff chemical sensing systems and methods use existing standoff chemical sensing technologies, but in contrast to existing improvements such as remote heat sources to heat a target material and thermally desorb chemical vapors in order to increase the concentration of trace chemical vapors in the air, uses acoustic excitation to drive trace chemical vapors from buried, low-volatility sources into the soil and from the soil into the air. By exposing trace vapors that have been protected from atmospheric dispersion, solar bleaching, and other weathering mechanisms, the present system both increases the concentration of trace chemical vapors in the air for standoff detection by an optical technology and the concentration or relative concentration of the predetermined trace chemical vapor itself.

The various aspects, embodiments, implementations, and variations described above are intended to be illustrative in nature, and are not intended to limit the scope of the invention. Any limitations to the invention will appear in the claims as allowed in view of the terms explicitly defined herein.

What is claimed is:

1. A system for detecting low-volatility chemicals buried below a ground surface, the system comprising:

an acoustic emitter positioned at a predetermined distance above the ground surface and configured to project a beam of acoustic energy toward the ground surface with a variable angle of incidence $\alpha$ so as to generate a surface wave;

a controller operatively connected to the acoustic emitter and configured to control the acoustic emitter to vary the angle of incidence of the acoustic beam within the variable angle of incidence $\alpha$;

an optical sensor configured for standoff sensing of a trace chemical vapor proximate the ground surface; and an indicator operatively connected to the optical sensor for indicating a detection of a predetermined trace chemical vapor by the optical sensor, wherein projection of the beam of acoustic energy causes a release of trace chemical vapors from under the ground surface, with said optical sensor sensing at least the predetermined trace chemical vapor, if present amongst the released trace chemical vapors.

2. The system of claim 1, wherein the variable angle of incidence may vary from a minimum angle of about 25 degrees to a maximum angle of about 37 degrees.

3. The system of claim 1, wherein the acoustic emitter is a directional acoustic emitter, and includes a motorized mount configured to alter a tilt of the acoustic emitter with respect to the ground surface.

4. The system of claim 1, wherein the acoustic emitter is a directionally agile acoustic emitter configured to electronically steer an acoustic beam in a vertical plane.

5. The system of claim 1, wherein the controller is configured to estimate a critical angle of incidence $\beta$ for coupling of the acoustic beam into the ground surface to generate the surface wave, and to control the acoustic emitter to project the acoustic beam toward the ground surface at the estimated critical angle of incidence $\beta$.

6. The system of claim 5, wherein the controller oscillates at least the acoustic beam within a predetermined subrange of the variable angle of incidence $\alpha$ centered around the estimated critical angle of incidence $\beta$.

7. The system of claim 5, wherein the controller is configured to receive at least one measured parameter which is incorporated into the estimate of the critical angle of incidence $\beta$.

8. The system of claim 7, wherein the at least one measured parameter is selected from a group consisting of a measured speed of sound in air, a measured speed of sound in the subsurface, a measured soil water content, a measured soil sand fraction, a measured soil clay fraction, and a measured soil silt fraction.

9. The system of claim 7, wherein the controller is configured to receive at least one observed parameter which is incorporated into the estimate of the critical angle of incidence $\beta$.

10. The system of claim 9, wherein the at least one observed parameter is selected from a group consisting of at an observed soil type and an observed soil water content.

11. The system of claim 7, wherein the controller is configured to receive hyperspectral or multispectral imagery of the ground surface, configured to analyze said imagery to measure at least one soil parameter which is incorporated into the estimate of the critical angle of incidence $\beta$.

12. The system of claim 7, further comprising a ground motion detector configured to measure the amplitude of surface waves generated by the acoustic emitter, wherein the ground motion detector is operatively connected to the controller to communicate said measurements to the controller, and wherein the controller is configured to estimate the critical angle of incidence $\beta$ by serially adapting prior estimates of the critical angle of incidence $\beta$ in response to said measurements.

13. The system of claim 12, wherein a first estimate of the critical angle of incidence $\beta$ is a default estimate, wherein a second estimate of the critical angle of incidence $\beta$ is a similar but different estimate with respect to the first estimate, and wherein the controller repeats an estimate-and-measure cycle to progress toward a critical angle value resulting in a maximum value of surface wave amplitude.

14. The system of claim 12, wherein the controller is configured to receive at least one measured or observed parameter which is incorporated into the estimate of the critical angle of incidence $\beta$, wherein a first estimate of the critical angle of incidence $\beta$ is based upon the at least one measured or observed parameter, wherein a second estimate of the critical angle of incidence $\beta$ is a similar but different estimate with respect to the first estimate, and wherein the controller repeats an estimate-and-measure cycle to progress toward a critical angle value resulting in a maximum value of surface wave amplitude.

15. The system of claim 1, wherein the optical sensor is configured for standoff sensing of a trace chemical vapor emitted from a buried bulk explosive charge, and the predetermined trace chemical vapor is a component of the buried bulk explosive charge.

16. A method for detecting low-volatility chemicals buried below a ground surface, the method comprising the ordered steps of:
(a) positioning an acoustic emitter at a predetermined distance d above the ground surface;
(b) emitting an acoustic beam from the acoustic emitter at at least one angle of incidence a so as to generate a surface wave;
(c) operating an optical sensor to detect at least a predetermined trace chemical vapor proximate the ensonified ground surface; and
(d) indicating, if the predetermined trace chemical vapor is detected, that the optical sensor has detected the buried low-volatility chemical, wherein emission of the acoustic beam causes a release of trace chemical vapors from under the ground surface, with said optical sensor detecting at least the predetermined trace chemical vapor if present amongst the released trace chemical vapors.

17. The method of claim 16, wherein the at least one angle of incidence is a variable angle of incidence $\alpha$, and wherein the emitting step includes oscillating the acoustic beam through at least a portion of the variable angle of incidence $\alpha$.

18. The method of claim 17, wherein the emitting step includes the step of estimating a critical angle of incidence $\beta$, and the at least a portion of the variable angle of incidence $\alpha$ is a predetermined subrange of the variable angle of incidence centered around the estimated critical angle of incidence $\beta$.

19. A method for detecting low-volatility chemicals buried below a ground surface, the method comprising the ordered steps of:
(a) positioning an acoustic emitter at a predetermined height above the ground surface;
(b) estimating a critical angle of incidence $\beta$, with the estimate being based upon at least one measured or observed parameter,
(c) emitting an acoustic wave from the acoustic emitter at the estimated critical angle of incidence $\beta$ toward the ground surface, whereby the acoustic wave is optimally coupled into a surface wave;
(d) scanning an optical sensor across the ground surface to detect a trace chemical vapor in the air above the ground surface; and
(e) indicating, if a predetermined trace chemical vapor is detected, that the optical sensor has detected the buried low-volatility chemical, wherein emission of the acoustic wave causes a release of trace chemical vapors from under the ground surface, with said optical sensor detecting at least the predetermined trace chemical vapor if present amongst the released trace chemical vapors.

20. The method of claim 19, wherein the emitting step includes oscillating the acoustic beam through a range of angles of incidence centered around the estimated critical angle of incidence $\beta$.

* * * * *